United States Patent
Mi et al.

(10) Patent No.: US 11,944,430 B2
(45) Date of Patent: Apr. 2, 2024

(54) MULTI-SENSOR DIABETES MANAGEMENT SYSTEM

(71) Applicant: Cardiac Pacemakers, Inc., St. Paul, MN (US)

(72) Inventors: Bin Mi, Arden Hills, MN (US); Pramodsingh Hirasingh Thakur, Woodbury, MN (US); Keith R. Maile, New Brighton, MN (US); Stephen B. Ruble, Lino Lakes, MN (US); Jonathan Bennett Shute, Minnetonka, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 173 days.

(21) Appl. No.: 16/664,315

(22) Filed: Oct. 25, 2019

(65) Prior Publication Data
US 2020/0129099 A1 Apr. 30, 2020

Related U.S. Application Data

(60) Provisional application No. 62/751,160, filed on Oct. 26, 2018.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0006* (2013.01); *A61B 5/0205* (2013.01);
(Continued)

(58) Field of Classification Search
CPC ... A61B 5/14532; A61B 5/366; A61B 5/0006; A61B 5/0205; A61B 5/0215;
(Continued)

(56) References Cited

U.S. PATENT DOCUMENTS

| 6,923,763 B1 | 8/2005 | Kovatchev et al. |
| 7,731,658 B2 * | 6/2010 | Dalal ............... A61M 5/1723 |
| | | 600/528 |

(Continued)

FOREIGN PATENT DOCUMENTS

| CN | 106137169 A | 11/2016 |
| KR | 20150131441 A | 11/2015 |
| WO | WO-2020086994 A1 | 4/2020 |

OTHER PUBLICATIONS

"International Application Serial No. PCT/US2019/058131, International Preliminary Report on Patentability dated May 6, 2021", 8 pgs.

(Continued)

*Primary Examiner* — Yi-Shan Yang
*Assistant Examiner* — Kyle W. Kretzer
(74) *Attorney, Agent, or Firm* — Schwegman Lundberg & Woessner, P.A

(57) ABSTRACT

Systems, devices, and methods for monitoring and assessing blood glucose level in a patient are discussed. An exemplary system receives physiologic information from a patient using an ambulatory medical device. The physiologic information is correlated to, and different from, a direct glucose level measurement. The system determines a glucose index indicative of an abnormal blood glucose level using the received physiologic information by the two or more physiologic sensors. The system may use the glucose index to initiate or adjust a therapy, or to trigger a glucose sensor, separate from the two or more physiologic sensors, to directly measure blood glucose concentration.

20 Claims, 7 Drawing Sheets

(51) Int. Cl.

| | |
|---|---|
| *A61B 5/0205* | (2006.01) |
| *A61B 5/0215* | (2006.01) |
| *A61B 5/053* | (2021.01) |
| *A61B 5/11* | (2006.01) |
| *A61B 5/366* | (2021.01) |
| *A61B 7/04* | (2006.01) |
| *G16H 50/30* | (2018.01) |

(52) U.S. Cl.
CPC .......... *A61B 5/0215* (2013.01); *A61B 5/1116* (2013.01); *A61B 5/366* (2021.01); *A61B 5/4839* (2013.01); *A61B 5/686* (2013.01); *A61B 7/045* (2013.01); *A61B 5/053* (2013.01); *G16H 50/30* (2018.01)

(58) Field of Classification Search
CPC ..... A61B 5/1116; A61B 5/4839; A61B 5/686; A61B 7/045; A61B 5/0816; A61B 5/02405; A61B 5/021; A61B 5/02; A61B 5/02007; A61B 5/053; G16H 50/30
See application file for complete search history.

(56) References Cited

U.S. PATENT DOCUMENTS

| | | | | |
|---|---|---|---|---|
| 8,019,410 | B1* | 9/2011 | Bharmi | A61B 5/0205 |
| | | | | 600/365 |
| 9,549,676 | B2* | 1/2017 | Sachanandani | G16H 50/30 |
| 9,622,664 | B2 | 4/2017 | An et al. | |
| 2012/0130212 | A1* | 5/2012 | Pluta | A61B 5/14532 |
| | | | | 600/345 |
| 2014/0221771 | A1* | 8/2014 | Wenzel | A61B 5/0006 |
| | | | | 600/301 |
| 2014/0323815 | A1* | 10/2014 | Han | A61B 5/0205 |
| | | | | 600/300 |
| 2015/0196224 | A1* | 7/2015 | Rusu | A61B 5/053 |
| | | | | 600/347 |
| 2017/0079533 | A1 | 3/2017 | Robinson et al. | |
| 2017/0311881 | A1* | 11/2017 | Jensen | A61B 5/4839 |

OTHER PUBLICATIONS

"International Application Serial No. PCT/US2019/058131, International Search Report dated Feb. 6, 2020", 5 pgs.

"International Application Serial No. PCT/US2019/058131, Written Opinion dated Feb. 6, 2020", 8 pgs.

Dobbin, Stephen, et al., "Management of atrial fibrillation in diabetes", Practical Diabetes vol. 35 No. 1, pp. 27-31.

Echouffo-Tcheugui, Justin B., et al., "Care Patterns and Outcomes in Atrial Fibrillation Patients With and Without Diabetes", JACC vol. 70, No. 11, Sep. 12, 2017, (1325-1335).

Mino, Lizbeth, et al., "Device Based Measures of Heart Rate Variability Are Different in Heart Failure Patients with Diabetes Mellitus", Journal of Cardiac Failure vol. 12 No. 6 Suppl. 2006, 1 page.

"European Application Serial No. 19805808.3, Response to Communication pursuant to Rules 161 and 162 filed Dec. 28, 2021", 10 pgs.

"European Application Serial No. 19805808.3, Communication Pursuant to Article 94(3) EPC dated Sep. 18, 2023", 6 pgs.

* cited by examiner

MULTI-SENSOR DIABETES MANAGEMENT SYSTEM

CLAIM OF PRIORITY

This application claims the benefit of priority under 35 U.S.C. § 119(e) of U.S. Provisional Patent Application Ser. No. 62/751,160, filed on Oct. 26, 2018, which is herein incorporated by reference in its entirety.

TECHNICAL FIELD

This document relates generally to medical devices, and more particularly, but not by way of limitation, to systems, devices, sensors, and methods for monitoring blood glucose and managing diabetes.

BACKGROUND

Diabetes is a common affliction in which a person's body does not produce or properly use insulin to convert sugar, starches and other substance into energy. The symptoms of diabetes are often not recognized, and it is estimated that about one-third of people with the disease do not realize they have it.

Diabetes is an important risk factor for cardiovascular morbidity. Compared to the general population, diabetes is more common within the patients who have congestive heart failure or cardiac arrhythmias such as atrial fibrillation (AF). Diabetic patients with AF, compared to those without diabetes, may have worse AF symptoms, lower quality of life, higher mortality and higher hospitalization rates, higher risk of sudden cardiac death, and higher risk of stroke. In patients with cardiac management device, it is estimated that approximately 11-13% of patients with pacemakers have diabetes, approximately 30-38% of patients having implantable cardioverter defibrillators have diabetes, and approximately 39-45% of patients having cardiac resynchronization therapy (CRT) devices have diabetes.

Monitoring blood glucose is important in diabetes management. Because diabetes prevents the patient's body from naturally regulating blood glucose, the diabetic patient must administer insulin in response to blood glucose levels. Failure to monitor blood glucose closely can result in dangerous conditions of hypoglycemia (blood glucose level too low) or hyperglycemia (blood glucose level too high). Complications of poor glucose control constitutes a significant portion of growing healthcare cost of diabetes management.

Hypoglycemia is a condition where the blood glucose level drops below some specified limits (e.g., 4 mmol/L or 72 mg/dL). Symptoms of hypoglycemia can range from dizziness, shakiness, or other discomfort to dangerous symptoms and conditions such as loss of consciousness, brain damage, or death. These symptoms generally result from insufficient glucose in the blood stream to the brain, thereby diminishing patient brain function. In diabetic patients, hypoglycemia can result from inappropriate dosing of insulin. Insulin affects the ability of the body's cells to use and consume glucose. Excessive insulin injection may cause cells to use too much glucose from the blood stream too quickly, resulting in glucose deficiency.

Hyperglycemia refers to high blood glucose level, a common problem for diabetic patients. Sustained high blood glucose levels can damage the blood vessels and multiple organs. Short-term symptoms of hyperglycemia can include frequent thirst, hunger, urination, as well as fatigue, weight loss, and other symptoms. Acute hyperglycemia can result in ketoacidosis, a condition where the liver breaks down fats and proteins in response to a perceived need for more glucose in the blood stream. For a diabetic patient, the problem is generally that the patient lacks adequate insulin to regulate glucose rather than the low blood glucose level. However, the body's response is to resort to drastic measures to increase the blood glucose level, and in doing so, the blood glucose level becomes elevated above a desired range. Sustained hyperglycemia can lead to hypertension, cardiomyopathy, atrial remodeling and atrial fibrillation, among other cardiovascular diseases.

SUMMARY

Discussed herein are systems and methods of determining a glucose index indicative of an abnormal blood glucose level using physiologic information received from a patient, such as collected by multiple wearable or implanted sensors that do not directly measure glucose level. The received physiologic information is correlated to, but different from, a direct glucose level measurement. The physiologic information may include cardiac electrical information, cardiac mechanical information (e.g., heart sounds information), bioimpedance information, patient autonomic response, blood pressure information, or respiration information. In some examples, the received physiologic information can include other physiologic information different from a direct glucose level measurement, such as from a wearable or implantable glucose monitor, etc. An early warning of abnormal glucose level can trigger additional glucose testing, or therapy initiation or titration. The multi-sensor glucose detection discussed herein may lead to more efficient diabetes management, improve patient outcome, and reduce overall healthcare cost.

Example 1 is a system comprising an ambulatory medical device configured to receive physiologic information correlated to, and different from, a direct glucose level measurement, where the physiologic information respectively sensed by two or more physiologic sensors from a patient, and an assessment circuit configured to determine a glucose index indicative of an abnormal blood glucose level using the received physiologic information sensed by the two or more physiologic sensors.

In Example 2, the subject matter of Example 1 optionally includes the two or more physiologic sensors that may be configured to sense respectively one of cardiac electrical information, cardiac mechanical information, bioimpedance information, patient autonomic response, blood pressure information, or respiration information.

In Example 3, the subject matter of any one or more of Examples 1-2 optionally includes the assessment circuit that can be configured to trigger a glucose sensor to directly measure a glucose level when the determined glucose index satisfies a condition, wherein the glucose sensor is separate from the two or more physiologic sensors.

In Example 4, the subject matter of Example 3 optionally includes an implantable or wearable glucose monitor communicatively coupled to the ambulatory medical device, the implantable glucose monitor including the glucose sensor configured to directly measure a glucose level when the determined glucose index satisfies a condition.

In Example 5, the subject matter of any one or more of Examples 3-4 optionally includes a calibration circuit configured to, using the measured glucose level, adjust a sensor configuration to sense physiologic information or calibrate an algorithm for generating the glucose index.

In Example 6, the subject matter of any one or more of Examples 1-5 optionally includes the ambulatory medical device that can include a cardiac sensor configured to receive cardiac electrical or mechanical information of the patient, and the assessment circuit that can be configured to determine the glucose index using the received cardiac electrical or mechanical information.

In Example 7, the subject matter of Example 6 optionally includes the cardiac sensor that can include electrodes configured to sense cardiac electrical information including one or more of a heart rate, a heart rate variability, a Q-T interval, or a cardiac arrhythmia, and the assessment circuit that can be configured to determine the glucose index using the sensed cardiac electrical information.

In Example 8, the subject matter of any one or more of Examples 1-7 optionally includes the ambulatory medical device that can include a heart sound sensor configured to receive heart sound information of the patient, and the assessment circuit that can be configured to determine the glucose index using the received heart sound information.

In Example 9, the subject matter of Example 8 optionally includes the assessment circuit that can be configured to generate one or more of first heart sound (S1) amplitude, second heart sound (S2) amplitude, or a cardiac timing interval using the received heart sound information, and to determine the glucose index using the generated one or more of S1 amplitude, S2 amplitude, or cardiac timing interval.

In Example 10, the subject matter of any one or more of Examples 1-9 optionally includes the ambulatory medical device that can include an impedance sensor configured to receive impedance information of the patient, and the assessment circuit that can be configured to determine the glucose index using the received impedance information.

In Example 11, the subject matter of Example 10 optionally includes the impedance sensor that can be configured to measure interstitial fluid impedance or blood impedance.

In Example 12, the subject matter of any one or more of Examples 1-11 optionally includes the ambulatory medical device that can include a pressure sensor configured to receive blood pressure information, and the assessment circuit that can be configured to determine the glucose index using the received blood pressure information.

In Example 13, the subject matter of any one or more of Examples 1-12 optionally includes a drug delivery device that can be configured to control delivery of the glucose therapy to the patient according to a delivery parameter, and the assessment circuit that can be configured to adjust the delivery parameter using the determined glucose index.

In Example 14, the subject matter of Example 13 optionally includes the delivery parameter that can include at least one of a dosage, a timing, or a drug.

In Example 15, the subject matter of any one or more of Examples 1-14 optionally includes a therapy circuit that can be configured to control a therapy to the patient according to a therapy parameter, and the assessment circuit that can be configured to adjust the therapy parameter using the determined glucose index.

Example 16 is a method comprising steps of: receiving physiologic information from the patient respectively sensed by two or more physiologic sensors from a patient, wherein the physiologic information is correlated to, and different from, a direct glucose level measurement, and determining a glucose index indicative of an abnormal blood glucose level using the received physiologic information sensed by the two or more physiologic sensors.

In Example 17, the subject matter of Example 16 optionally includes triggering a glucose sensor to directly measure a glucose level when the determined glucose index satisfies a condition, wherein the glucose sensor is separate from the two or more physiologic sensors.

In Example 18, the subject matter of Example 17 optionally includes adjusting a sensor configuration to sense physiologic information or calibrating an algorithm for generating the glucose index using the measured glucose level.

In Example 19, the subject matter of any one or more of Examples 16-18 optionally includes delivering a glucose therapy to the patient according to a delivery parameter, and adjusting the delivery parameter using the determined glucose index.

In Example 20, the subject matter of any one or more of Examples 16-19 optionally includes delivering electrostimulation to the patient according to a therapy parameter, and adjusting the therapy parameter using the determined glucose index.

In Example 21, the subject matter of any one or more of Examples 16-20 optionally includes the received physiologic information that can include one or more of cardiac information, heart sound information, respiration information, impedance information, pressure information, or activity or posture information.

In Example 22, the subject matter of any one or more of Examples 16-21 optionally includes generating a composite risk score using the received physiologic information respectively received from two or more physiologic sensors, and determining the glucose index using the composite risk score.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
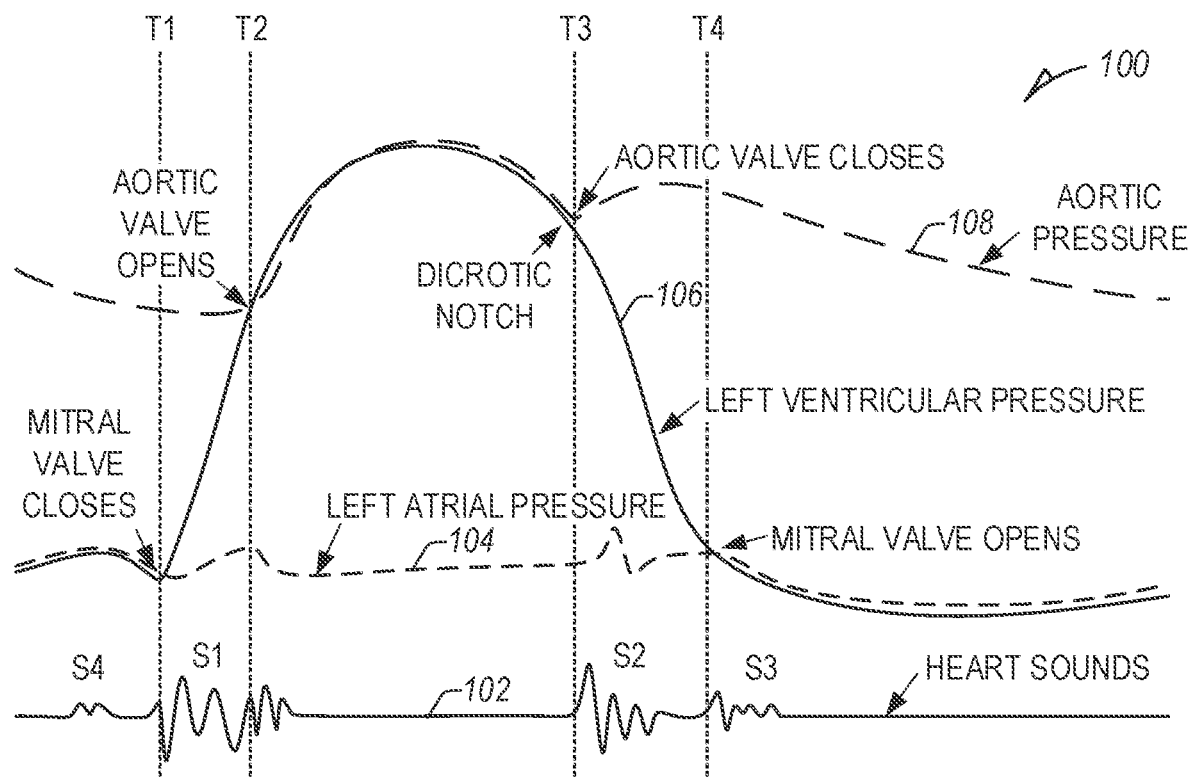
FIG. 1 illustrates an example of multiple physiologic parameters and timing relationship therebetween.

Close monitoring of blood glucose level is important for diabetes management. However, continuous blood glucose monitoring can be technically difficult. Conventional glucometer analyzes a small blood sample, such as obtained by via finger prick, for glucose content. This requires patient involvement, and can be inconvenient, unpleasant, or painful. As a result, patient compliance with the testing protocol can be poor for some patients. Additionally, finger prick is generally carried out intermittently rather than continuously (typically 2-4 times per day), such that the sporadic glucose readings may not adequately reflect patient glucose fluctuations between the readings.

Subcutaneous or implantable blood glucose monitors have been used to monitor blood glucose level continuously, thus also referred to as continuous glucose monitors (CGMs). The CGMs have overcome some drawbacks associated with finger prick; however, despite extensive research and development efforts, the long-term functionality of CGMs may still suffer from stability, biofouling, or degradation.

Moreover, CGMs typically measure glucose levels using patient interstitial fluid rather than directly from blood sample. The interstitial glucose level generally lags behind the blood glucose value (e.g., approximately a 15-minute lag), partly due to the physiologic process of transporting the glucose molecules from the blood capillaries through the interstitial volume to the surface of the glucose sensor. This may compromise the accuracy and timeliness of detecting hypoglycemia condition and result in critical complications or death, particularly in patients having rapidly changing glucose levels. Additionally, although CGM can make glucose management easier, it generally requires frequent calibration with a blood glucose test such as finger prick. CGMs and procedures of implantation or placement generally also involve relatively higher costs. Furthermore, CGMs typically generate a large amount of blood glucose readings and other data that require clinician review, which can be a high clinical and financial burden in diabetic patient care.

For at least these reasons, improved techniques are needed for monitoring blood glucose level and managing diabetic patients. Timely and accurate detection of abnormal glucose level, particularly in an ambulatory setting, may allow appropriate therapy intervention or titration and help prevent adverse patient outcome. The present inventor has recognized, among other things, that monitoring of blood glucose level using an ambulatory medical device (e.g., a wearable or implantable device) that detects an indication of abnormal blood glucose level without direct measurement of blood glucose level, can enable early detection and better management of diabetes.

One or more existing ambulatory medical device sensors can be used to detect early clinical or subclinical manifestations of abnormal blood glucose level, such as in response to a diabetic therapy (e.g., insulin injection or insulin infusion pump, or electrostimulation therapy to treat certain complications of diabetes such as neuropathic symptoms). The one or more ambulatory medical device sensors do not directly measure glucose level from blood or interstitial fluid samples, but instead sense physiologic information that is correlated to, but different from, a direct glucose level measurement. Examples of the received information may include cardiac electrical information, cardiac mechanical information (e.g., heart sounds information), bioimpedance information, patient autonomic response, blood pressure information, or respiration information, etc. Such information may be used to pre-screen patients for further medical intervention or therapy optimization (e.g., drug titration or timing, etc.). The advancements discussed herein can provide for early detection of treatable conditions, in certain examples providing additional use for existing sensors, reducing sensor cost, and enabling earlier intervention, improving patient outcomes, and reducing overall medical system costs. The systems and methods described herein, in certain examples, represent an improved form of blood glucose detection and patient intervention over existing techniques. In certain examples, patients can be monitored, and the patient, caregiver, clinician, or one or more other system or user can be alerted to a change in patient condition indicative of hyper- or hypoglycemia. In other examples, the systems and methods described herein can provide intervention or therapy optimization recommendation (e.g., dosage or timing change, change in prescribed drug, etc.), or can directly provide or alter a therapy to the patient.

FIG. 1 illustrates an exemplary relationship 100 among various physiologic parameters measured from a subject. Some or all of the physiologic parameters shown in FIG. 1 may be monitored using ambulatory sensors during and/or after patient receiving therapy (e.g., insulin therapy), and be used to detect and assess hyper- or hypoglycemia. By way of example and not limitation, the physiologic parameters may include heart sounds 102, including first, second, third, and fourth heart sounds (S1, S2, S3, and S4), left atrial pressure 104, left ventricular pressure 106, and aortic pressure 108, among other parameters.

At a first time (T1), a mitral valve closes, marking a rise in left ventricular pressure 106, and the start of the first heart sound (S1) and systole, or ventricular contraction. At a second time (T2), an aortic valve opens, marking a rise in aortic pressure 108 and continuing S1. S1 is caused by closure of the atrioventricular (AV) valves, including the mitral and tricuspid valves, and can be used to monitor heart contractility.

At a third time (T3), an aortic valve closes, causing a dicrotic notch in the aortic pressure 108 and the second heart sound (S2), and marking the end of systole, or ventricular contraction, and the beginning of diastole, or ventricular relaxation. S2 can be used to monitor blood pressure. At a fourth time (T4), the mitral valve opens, and the left atrial pressure 104 drops. An abrupt halt of early diastolic filling can cause the third heart sound (S3), which can be indicative of (or an early sign of) heart failure (HF). Vibrations due to atrial kick can cause the fourth heart sound (S4), which can be used to monitor ventricular compliance.

Systolic time intervals, such as pre-ejection period (PEP) or left ventricular ejection time (LVET) can be indicative of clinically relevant information, including contractility, arrhythmia, Q-T prolongation (with electrogram (EGM) information), etc. The PEP can be measured from a Q wave of an EGM to the time of the aortic valve opening, T2 in FIG. 1. The LVET can include a time between the aortic valve opening, T2, and the aortic valve closing, T3. In other examples, one or more systolic time intervals can be detected and used to detect physiologic information of a patient (e.g., PEP/LVET, one or more mechanical, electrical, or mechanical-electrical time intervals, etc.).

Ambulatory medical devices, including implantable, leadless, or wearable medical devices configured to monitor, detect, or treat various cardiac conditions associated with a reduced ability of a heart to deliver blood to a body, such as heart failure (HF), arrhythmias, hypertension, etc. Various ambulatory medical devices can be implanted in a patient's body or otherwise positioned on or about the patient to monitor patient physiologic information, such as heart sounds, respiration (e.g., respiration rate, tidal volume, etc.), impedance (e.g., thoracic impedance), pressure, cardiac activity (e.g., heart rate (HR)), physical activity, posture, or one or more other physiologic parameters of a patient, or to provide electrical stimulation or one or more other therapies or treatments to optimize or control contractions of the heart.

Traditional cardiac rhythm management (CRM) devices, such as pacemakers, defibrillators, or cardiac monitors, include implanted devices (e.g., implantable cardioverter-defibrillators (ICDs), etc.), subcutaneous devices (e.g., subcutaneous ICDs (S-ICDs), etc.), or one or more other devices configured to be implanted within in a chest of a patient, or under the skin of the patient, in certain examples, having one or more leads to position one or more electrodes or other sensors at various locations in the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient, for example, using one or more therapy circuits.

Leadless cardiac pacemakers (LCP) include small (e.g., smaller than traditional implantable CRM devices), self-contained devices configured to detect physiologic information from or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Wearable or external medical sensors or devices can be configured to detect or monitor physiologic information of the patient without required implant or an in-patient procedure for placement, battery replacement, or repair. In some cases, such wearable or external medical devices can also provide an electrical stimulation or other therapy to the patient.

Determination of one or more patient conditions (e.g., hypertension, HF, etc.), or risk stratification for one or more patient conditions, often requires some initial assessment time to establish a baseline level or condition from one or more sensors or physiologic information from which a detected deviation is indicative of the patient condition, or risk of patient condition or future adverse medical event (e.g., the risk of the patient experiencing a heart failure event (HFE) within a following period, etc.). Changes in physiologic information can be aggregated and weighted using one or more patient-specific stratifiers. However, such changes and risk stratification are often associated with one or more thresholds, for example, having a clinical sensitivity and specificity across a target population with respect to a specific condition (e.g., HF), etc., and one or more specific time periods, such as daily values, short-term averages (e.g., daily values aggregated over a number of days), long-term averages (e.g., daily values aggregated over a number of short-term periods or a greater number of days (sometimes different days than used for the short-term average)), etc.

For example, a multi-sensor algorithm has been demonstrated to predict HF events in patients with a high sensitivity and low false positive rate using physiologic information detected from one or more implanted or ambulatory medical devices. In other examples, such algorithm can be applied to one or more other medical events, such as hypertension or one or more conditions associated with hypertension, etc. The multi-sensor algorithm can determine a composite physiologic parameter using one or more of the following physiologic information: heart sounds (e.g., a first heart sound (S1), a second heart sound (S2), a third heart sound (S3), a fourth heart sound (S4), heart-sounds related time intervals, etc.), thoracic impedance (TI), respiratory rate (RR), rapid shallow breathing index (RSBI), heart rate (HR) (e.g., nighttime HR), activity, posture, cardiac activity, pressure, etc.

In certain examples, such multi-sensor algorithm can be adjusted using a determined patient risk level (e.g., a stratifier). The combination of or weight of respective primary and secondary sensors used to determine the composite physiologic parameter can be adjusted using the determined patient risk level. For example, if the determined patient risk level indicates a low risk of a worsening physiologic condition, the composite physiologic parameter can be determined using one or more primary sensors (and not one or more secondary sensors). If the determined patient risk level indicates a medium or high risk of worsening heart failure, the composite physiologic parameter can be determined using the primary sensors and a combination of the secondary sensors, depending on the determined patient risk level. In an example, the multi-sensory algorithm can determine a glucose index indicative of an abnormal blood glucose level, and provide an alert, a recommended intervention or change in parameter or therapy, or directly change or provide a therapy to the patient.

In an example, S1 amplitude can be a marker of contractile function (e.g., a decrease in S1 amplitude, or a decrease in the change of S1 amplitude, can be indicative of reduced contractility or contractile function, and vice versa, etc.). Systolic time intervals (e.g., PEP, PEP/LVET, etc.) can be indicative of contractile function (e.g., an increase in PEP or PEP/LVET can be indicative of a decrease in contractility). Hyperglycemia, such as due to insulin discontinuation, may be associated with an increase in myocardia contractility in type II diabetic patients without or without HF. An increase in S1 amplitude or a decrease in a systolic time interval indicates increased myocardial contractility, and can used to detect or provide early warning of hyperglycemia.

In an example, S2 amplitude can be a marker of afterload changes (e.g., an increase in S2 can be indicative of increased afterload, and a reduction of stroke volume, etc.) As afterload increases, cardiac output decreases. This may be accompanied by hypotension (reduced blood pressure). Changes in blood glucose levels may affect myocardial contractility and stiffness. Accordingly, by the Frank-Starling mechanism, the changes in myocardial contractility and stiffness may affect cardiac relaxation and diastolic function, which are two contributors to the S2 sound. Thus, changes in blood glucose level can change the S2 heart sound, including its intensity (e.g., peak S2 amplitude) and its duration. In some examples, time intervals between S1 and S2 heart sounds (S1-S2 interval) can be used to detect hyper- or hypoglycemia. For example, a patient in a hypoglycemic state tends to exhibit lengthening of S1-S2 interval; while a patient in a hyperglycemic state tends to exhibit little or no change in of S1-S2 interval, A commonly assigned U.S. Pat. No. 7,731,658 to Dalal et al. discusses apparatus and methods for determining hypoglycemic or hyperglycemic condition in a patient using heart sounds sensor signals, including amplitude of S1, S2, S3 heart sounds and S1-S2 interval, the subject matter of which is incorporated herein by reference in its entirety.

In an example, S3 amplitude, thoracic impedance, or respiratory measurements can be used to track fluid or preload changes, and further can be early indicators of worsening heart failure (WHF). For example, an increase in S3 (or S4) can be indicative of worsening of cardiac diastolic function, associated with lung fluid accumulation. Further, changes in respiratory rate (e.g., median respiratory rate trend (RRT) (minimally impacted by activity or exercise), etc.), tidal volume, rapid shallow breathing index (RSBI), dyspnea, tachypnea, hypoxia, heart rate (e.g., resting heart rate), or combinations thereof, can be indicative of decreased cardiac function (e.g., an increased respiratory rate, tidal volume, or heart rate can be indicative of decreased cardiac output). Abnormal blood glucose level may be associated with pulmonary edema, dyspnea, or pneumonitis, which may exacerbate heart failure or other cardiac conditions. Accordingly, S3, thoracic impedance, or directly measured respiratory parameters may be used as an early indicator of abnormal glucose level. In various examples, HS morphology, such as morphologies of S1 or S2 heart sounds, may also be used to detect abnormality in blood glucose level.

In an example, one or more electrical, mechanical, or electrical-mechanical intervals can be used to track cardiac output or one or more other conditions, such as Q-T prolongation, etc., indicative of a decrease in cardiac output. For example, one or more of a Q-T interval, an R-T interval, an R-S2 interval, or one or more other electrical, mechanical, or electrical-mechanical intervals can be indicative of Q-T prolongation (e.g., an increase in one or more of the Q-T, R-T, or R-S2 interval can be indicative of an increase in Q-T prolongation, which can be indicative of arrhythmia, or a decrease in cardiac output, etc.), which can be indicative of an increased likelihood of abnormal blood glucose level.

In an example, the systems and methods described herein can be used to monitor patient physiologic responses to diabetic treatment, adjust or optimize diabetes therapy (e.g., drug injections, biological therapy, electrostimulation therapy, or other diabetic treatment options). In one example, the systems discussed herein may provide an alert to a clinical of an abnormal glucose level in a patient, such that the clinician may initiate or adjust a therapy accordingly. In another example, the systems and methods include automatic initiation or titration of diabetes therapy using a detected glucose index, such as controlling a drug delivery system (e.g., an insulin pump) to adjust dosage, timing, drug type, or other delivery parameters. In some examples, the present systems and methods may control an electrostimulation system (e.g. an implantable or wearable electrostimulator) to adjust one or more stimulation parameters. Examples of the electrostimulation therapy may include gastric stimulation that mediates the signal of stomach contraction triggered by food intake, neuromuscular stimulation for treating diabetic neuropathy (including nerve damage in various tissue) such as through pain relief and accelerated healing, or vagus nerve stimulation for regulating blood glucose level, among other therapy modalities.

In an example, if a patient has an existing cardiac monitor or ambulatory medical device, the existing devices may switch modes to implement the systems and methods described herein. In other examples, one or more additional ambulatory medical devices can be deployed to perform the systems and methods described herein.

Figure 2:
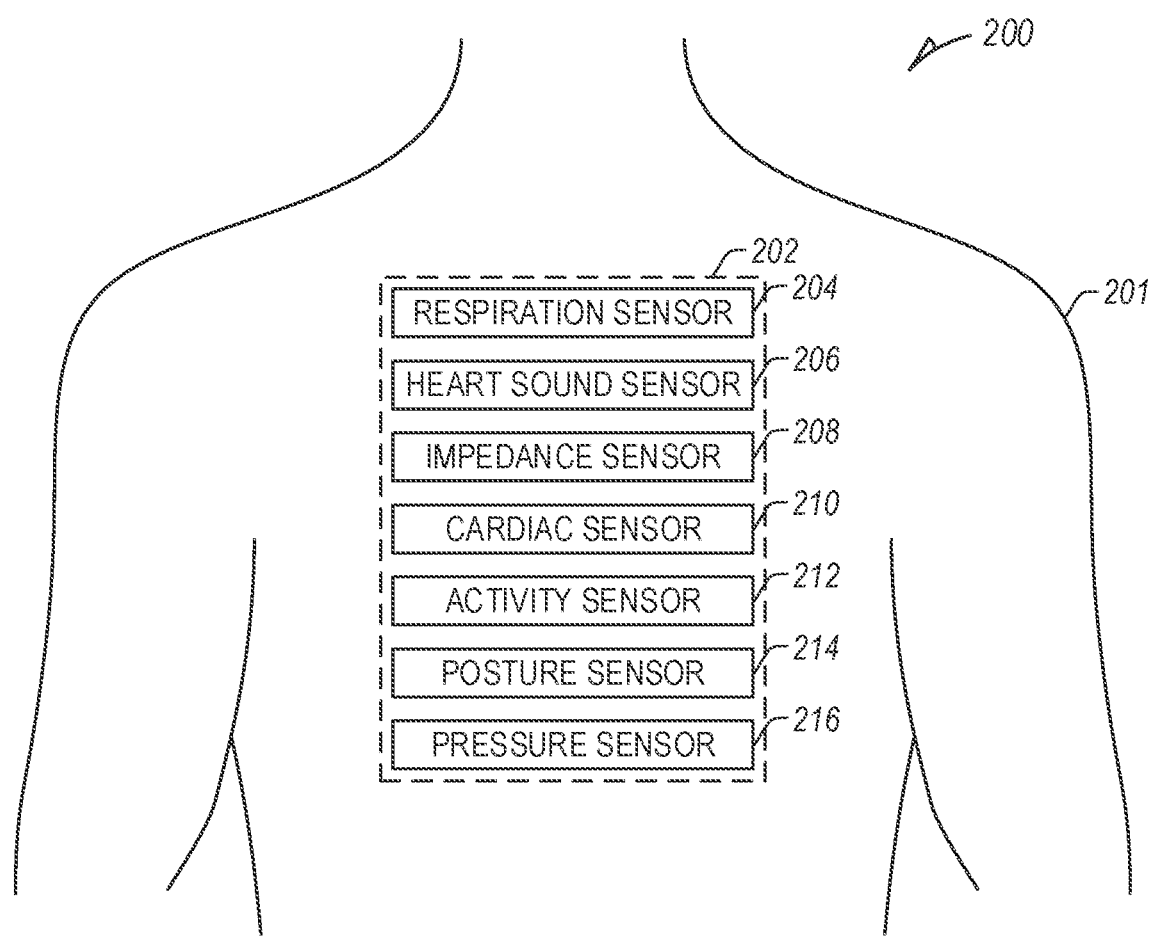
FIG. 2 illustrates an example system including an ambulatory medical device (AMD) configured to sense or detect information from a patient.

FIG. 2 illustrates an example system 200 including an ambulatory medical device (AMD) 202 configured to sense or detect information from a patient 201. In an example, the AMD 202 can include an implantable medical device (IMD), a subcutaneous or leadless medical device, a wearable or external medical device, or one or more other implantable or external medical devices or patient monitors. The AMD 202 can include a single device, or a plurality of medical devices or monitors configured to detect patient information.

The AMD 202 can include one or more sensors configured to receive physiologic information of a patient 201. In an example, the AMD 202 can include one or more physiologic sensors, such as a respiration sensor 204, a heart sound sensor 206, an impedance sensor 208, a cardiac sensor 210, an activity sensor 212, a posture sensor 214, and a pressure sensor 216. These sensors may sense respectively physiologic information that is correlated to, but different from, a direct glucose level measurement such as provided by a glucose sensor. In some examples, the one or more sensors may respectively detect patient physiologic responses to changes in blood glucose levels (e.g., hyper- or hypoglycemia), including one or more of cardiac response, autonomic response, adrenal response, respiratory response, or tissue impedance (e.g., blood or interstitial fluid impedance) response to changes in blood glucose level.

The respiration sensor 204 can be configured to receive respiration information, including but not limited to a respiration rate (RR), a respiration volume (tidal volume), an RSBI, indicators of dyspnea, tachypnea, respiration pattern, etc. Such respiration information may be used to detect respiratory response to abnormal blood glucose level.

The heart sound sensor 206 may take a form of an accelerometer, a microphone sensor, or a gyroscope sensor, placed on the body surface, a subcutaneous location (e.g., pectoral or abdominal location), epicardial or endocardial location, or situated on an implantable lead. The heart sound sensor 206 can sense cardiac vibration, sound, motion, or endocardial or epicardial acceleration, and can be configured to receive heart sound information, such as intensity (e.g., amplitudes) of one or more of S1, S2, S3, or S4 heart sound components, and systolic time intervals measured using at least one heart sound component. Such heart sounds information may be used to detect cardiac response to abnormal blood glucose level, such as changes in cardiac function (e.g., contractility, ejection fraction, systolic blood pressure, and cardiac output), cardiac arrhythmias, and WHF, among others.

The impedance sensor 208 can be configured to receive impedance information, such as interstitial fluid impedance from a pectoral location, abdominal location, or other body locations; or blood impedance from a blood vessel or inside a heart chamber. An example of measuring the impedance includes an electrochemical impedance spectroscopy method. Impedance measured at certain frequencies, approximately within 1-1.5 KHz in an example, may be correlated with blood glucose concentration.

The cardiac sensor 210 can be configured to receive cardiac electrical information, such as an electrocardiograph (ECG), a subcutaneous ECG, or an intracardiac electrogram (EGM). The sympathetic and parasympathetic nervous system may both be affected by changes in blood glucose levels, potentially leading to cardiac autonomic neuropathy characterized by an altered cardiac rhythm due to the initial changes in the parasympathetic, followed by sympathetic, modulation of cardiac rhythm. Autonomic response to abnormal glucose level may be measured using heart rate variability (HRV). For example, hypoglycemia may be associated with increased heart rate and abnormalities in high- and low-frequency HRV. Cardiac parameters such as heart rate, heart rate variability, cardiac synchrony, cardiac arrhythmias, conduction abnormalities, may be generated and used to detect one or more of symptoms associated with the abnormal blood glucose level.

The activity sensor 212 can be configured to receive information about a physical motion (e.g., activity, steps, etc.), and the posture sensor 214 can be configured to receive posture or position information. Changes in physical activity or changes in posture may be indicative of abnormal blood glucose level, or patient habitual change secondary to inadequate glucose regulation, such as development or worsening of one or more comorbidities including hypertension, cardiovascular disease, kidney disease, hyperlipidemia, obesity, among others. Information about patient physical activity, motion, posture, or position change may be used to trigger the operations of one or more other physiologic sensors. For example, heart sounds, impedance, or pressure data may be acquired when certain physical activity level or a specified posture is detected.

The pressure sensor 216 may be configured to receive pressure information. In an example, the pressure sensor 216 is a blood pressure sensor configured to sense blood pressure. Acute hyperglycemia may significantly increases systolic and diastolic blood pressures. Acute hypoglycemia provokes sympatho-adrenal activation and release of epinephrine, which in turn stimulates hemodynamic changes by increasing heart rate and peripheral systolic blood pressure, reducing central blood pressure and peripheral arterial resistance, and increasing myocardial contractility, stroke volume and cardiac output. Blood pressure changes, among other hemodynamic changes, may be used to detect abnormal blood glucose level, such as acute hyperglycemia or hypoglycemia.

In various examples, the AMD 202 may include circuitry, or a microprocessor, that can generate a composite risk score using the physiologic information respectively sensed by the two or more of the physiologic sensors 204-216. A glucose index may be determined using the composite risk score. In some examples, the AMD 202 may generate two or more intermediate risk scores representing various physiologic reactions to abnormal glucose level, and generate a composite risk score using a combination of two or more of the generated intermediate risk scores. By way of non-limiting example, the intermediate risk scores may include: a cardiac risk score computed using statistical measurements (e.g., baseline change over a specific time, mean, variance, or other first, second, or higher-order statics) or morphological changes of physiologic parameters including HR, arrhythmias, HS parameters (e.g., S1, S2, S3, S4, or systolic time intervals); an autonomic risk score computed using statistical measurements or morphological changes of physiologic parameters such as HRV; an adrenal risk score computed using statistical measurements or morphological changes of physiologic parameters including systolic BP, diastolic BP, cardiac pressure, peripheral arterial resistance, among others; and an impedance risk score computed using statistical measurements or morphological changes of physiologic parameters including interstitial fluid impedance such as measured at a pectoral or abdominal region, and blood impedance from a blood vessel or inside a heart chamber.

Figure 3:
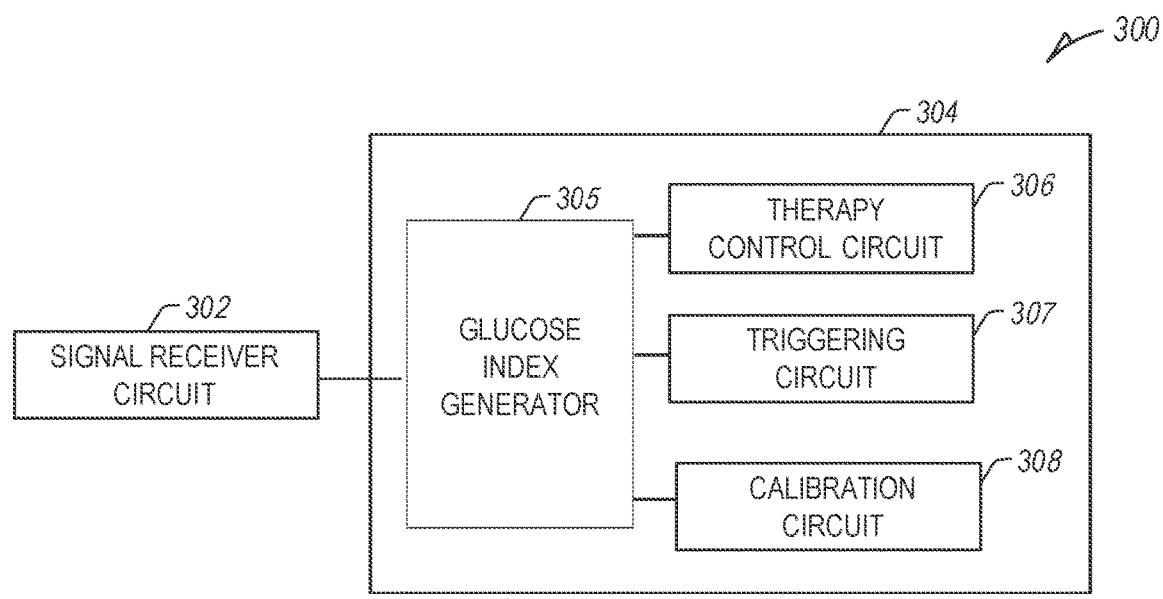
FIG. 3 illustrates a portion of an exemplary glucose management system including a signal receiver circuit and an assessment circuit.

FIG. 3 illustrates a portion of an exemplary glucose management system (e.g., a medical device, etc.) 300, which includes a signal receiver circuit 302 and an assessment circuit 304. The signal receiver circuit 302 can be configured to receive patient information, such as physiologic information of a patient (or a group of patients) from one or more of the physiologic sensors 204-216 as discussed above with reference to FIG. 2. The assessment circuit 304 includes one or more of a glucose index generator 305, a therapy control circuit 306, a triggering circuit 307, or a calibration circuit 308. The glucose index generator 305 can be configured to receive information from the signal receiver circuit 302, determine an glucose index indicative of an abnormal blood glucose level using the received physiologic information, and determine one or more diagnostic or therapeutic parameters (e.g., composite physiologic parameters, stratifiers, one or more pacing parameters, etc.), such as described herein. In an example, the glucose index generator 305 may compare the glucose index to one or more thresholds, and determines an indication of hyperglycemia if the glucose index exceeds a first threshold, or an indication of hypoglycemia if the glucose index falls below a second threshold. The individualized first and second thresholds may be determined using risk factor, diabetes history, or other medical conditions of a patient.

The therapy control circuit 306 can determine an optimized therapy delivery parameter using the determined glucose index, such as drug type, dosage, or timing of drug therapy (e.g., insulin injection or an ambulatory insulin pump). Additionally or alternatively, the therapy control circuit 306 may determine an optimized electrostimulation parameter using the determined glucose index, such as pulse amplitude, pulse width, pulse shape, timing, or duration of electrostimulation therapy. In an example, the assessment circuit 304 can generate a composite risk score using the received physiologic information, and to determine the glucose index using the composite risk score. The composite risk score can be a linear or a nonlinear combination (e.g., weighted combination) of the received physiologic information from the two or more sensors.

The triggering circuit 307 can be configured to trigger a glucose sensor to perform a glucose test when the determined glucose index indicates an abnormal blood glucose level, such as to confirm or reject the multi-sensor based determination of hyper- or hypoglycemia. In an example, the glucose sensor can be a wearable or subcutaneously implantable sensor of a continuous glucose monitor (CGM) system. The glucose sensor can be placed under the skin of the belly, or it can be adhered to the back of arm, to directly measure and generate readings of the glucose level. A transmitter on the sensor then sends the information to a wireless wearable monitor. In an example, the glucose sensor can be an invasive sensor configured to measure glucose level directly from blood or interstitial fluid. In another example, the glucose sensor can be a wearable glucose-monitoring patch configured to attach to the skin and measure glucose level directly from the interstitial fluid within the body-hair follicles. Alternatively, the CGM can include a non-invasive glucose sensor configured to measure glucose level noninvasively, such as by means of fluorescence, absorption spectroscopy, near-infrared absorption spectroscopy, or photoacoustic spectroscopy, among others.

The assessment circuit 304 can provide an output to a user (e.g., a patient, a caregiver, or a clinician), such as to a display or one or more other user interface, the output including a score, a trend, or other indication. In an example, the output can include an indication of abnormality in patient glucose level. The output may include recommendations for taking further glucose test, consulting with caregiver, taking or adjusting medication (e.g., oral medication or insulin injections), lifestyle management, comorbidity assessment, management or prevention of major adverse cardiovascular events and/or cardiovascular mortality, among other standards of medical care in diabetes. In other examples, the assessment circuit 304 can be configured to provide an output to another circuit, machine, or process, such as to control, adjust, or cease a therapy of a medical device, a drug delivery system, etc. In an example, the triggering circuit 307 may generate an alert or notification to warn a clinician or a caregiver of the determined abnormality in the glucose level, and recommend a glucose test (e.g., a finger prick test, or glucose strip test using a glucometer to measure glucose concentration in a blood sample). The alert or notification may include audio, text, graph, animation, or other visual or audiovisual formats. In some examples, the alert or notification, optionally along with other sensor measurements and patient information, may be sent over to a patient management system or a mobile device.

The calibration circuit 308 can be configured to calibrate the glucose index generator 305 using the glucose concentration measurements obtained from a finger prick test, blood draw and glucose strip test, or readings from a CGM. In an example, based on glucose concentration measurement, the calibration circuit 308 can be configured to adjust sensor operations (e.g., sensor configuration, timing, sampling rate, duration) for collecting physiologic information, such as one or more of the sensors 204-216. Additionally or alternatively, based on the glucose concentration measurement, the calibration circuit 308 can be configured to adjust an algorithm used by the glucose index generator 305 to determine the glucose index, such as by adjusting the weights for individual sensors, or the method of combining the sensor measurements to generate a composite risk score.

Figure 4:
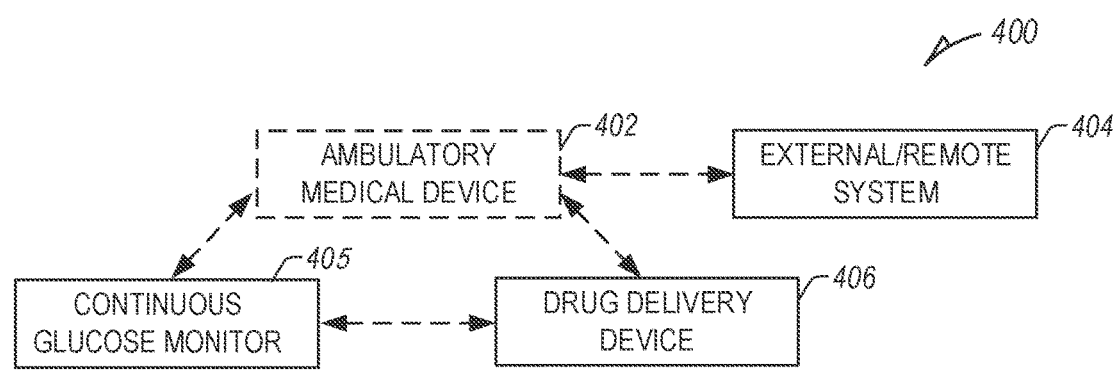
FIG. 4 illustrates an exemplary glucose management system including an ambulatory medical device (AMD) coupled to an external or remote system, such as an external programmer.

FIG. 4 illustrates an exemplary glucose management system 400 including an ambulatory medical device (AMD) 402 coupled to an external or remote system 404 (e.g., an external programmer), a continuous glucose monitor (CGM) 405, and a drug delivery device 406. The AMD 402 can be an implantable device, an external device, or a combination or permutation of one or more implantable or external devices. In an example, one or more of the signal receiver circuit 302 or the assessment circuit 304 can be located in the AMD 402, or the remote system 404. In an example, the AMD 402 can include a therapy circuit configured to generate an electrostimulation therapy (e.g., cardiac pacing or defibrillation pulses, neurostimulation pulses, neuromuscular stimulation pulses, or stimulation of other target tissues) to be provided to a patient. The remote system 404 can include a specialized device configured to interact with the AMD 402, including to program or receive information from the AMD 402. One or more of the AMD 402 or the remote system 404 may determine a glucose index, or a composite risk score indicative of abnormal blood glucose level, using the received physiologic information. In response to the determined glucose index satisfying a specific condition such as exceeding a threshold or falling within a specific range, the AMD 402 or the remote system 404 may adjust one or more therapy parameter using the determined glucose index. Alternatively, the AMD 402 or the remote system 404 may notify patient, caregiver, or physician to administer or modify treatment (e.g., oral medication, insulin injection, insulin pump, or electrostimulation therapy). For a particular patient, the thresholds could be personally determined based on his risk factor, diabetes history and other medical conditions. The therapy circuit in the AMD 402 may generate and deliver electrostimulation therapy according to the adjusted therapy parameter.

The continuous glucose monitor (CGM) 405 may include sensors configured to monitor glucose concentration invasively or noninvasively. The continuous glucose monitor 405 may be communicatively coupled to the ambulatory medical device 402, such as via a wired connection or a wireless communication link. When the ambulatory medical device 402 determines a glucose index indicative of an abnormal blood glucose level, it can trigger the CGM to measure the glucose concentration to confirm the determined abnormal glucose level. The ambulatory medical device 402 may receive from the CGM the glucose measurements to calibrate the glucose index generation, such as by adjusting an algorithm to compute the glucose index using the physiologic information obtained from multiple sensors (e.g., sensors 204-216 as illustrated in FIG. 2), or to adjust sensor operations (e.g., sensing configuration, timing, sampling rate, duration, etc.) to collect the physiologic information.

The drug delivery device 406 can be configured to send information to, or receive information from, one or both of the AMD 402 or the remote system 404. The drug delivery device 406 can be configured to deliver one or more drugs to a patient. In an example, the drug delivery device 406 can include an insulin pump to automatically provide a prescribed dosage of insulin to the patient to regulate the blood glucose level when the ambulatory medical device 402 determines that the glucose index satisfies a specific condition indicating hyperglycemia in a patient. The drug delivery device 406 may additionally or alternatively administer or adjust insulin dosage in response to the glucose measurement provided by the CGM 405 satisfying a specific condition. In some examples, the delivered drug may include drugs to alleviate the symptoms, complications, or other adverse events associated with hyper- or hypoglycemia, such as pain-relief drugs to remedy diabetic neuropathy. In an example, the AMD 402 or the remote system 404 can be configured to control one or more parameters of the drug delivery system 406, such as drug type, dosage, or timing of the drug therapy, using the glucose index generated from the received physiologic information.

Figure 5:
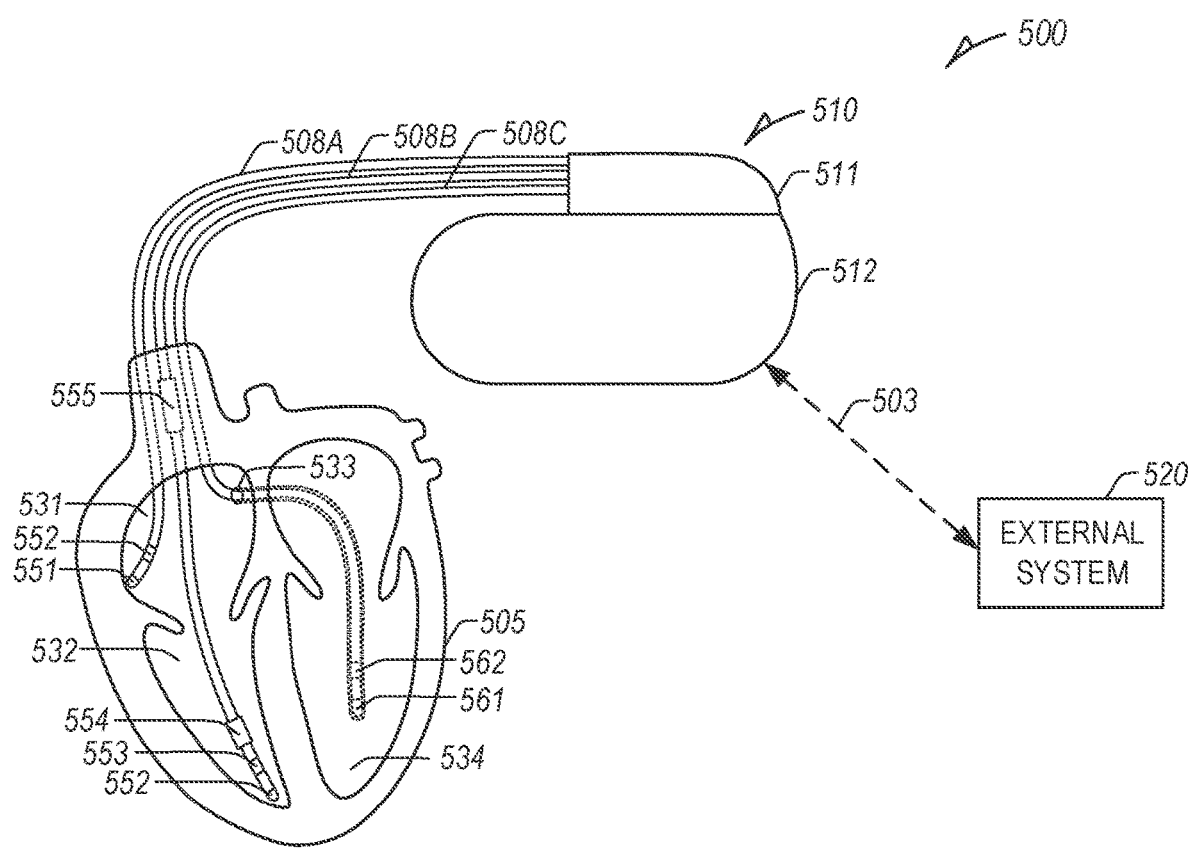
FIG. 5 illustrates an example of a Cardiac Rhythm Management (CRM) system and portions of an environment in which the CRM system can operate.

FIG. 5 illustrates an example of a Cardiac Rhythm Management (CRM) system 500 and portions of an environment in which the CRM system 500 can operate. The CRM system 500 can include an ambulatory medical device, such as an implantable medical device (IMD) 510 that can be electrically coupled to a heart 505 such as through one or more leads 508A-C coupled to the IMD 510 using a header 511, and an external system 520 that can communicate with the IMD 510 such as via a communication link 503. The IMD 510 may include an implantable cardiac device such as a pacemaker, an implantable cardioverter-defibrillator (ICD), or a cardiac resynchronization therapy defibrillator (CRT-D). The IMD 510 can include one or more monitoring or therapeutic devices such as a subcutaneously implanted device, a wearable external device, a neural stimulator, a drug delivery device, a biological therapy device, or one or more other ambulatory medical devices. The IMD 510 may be coupled to, or may be substituted by a monitoring medical device such as a bedside or other external monitor.

The IMD 510 can include a hermetically sealed can 512 that can house an electronic circuit that can sense a physiologic signal in the heart 505 and can deliver one or more therapeutic electrical pulses to a target region, such as in the heart, such as through one or more leads 508A-C. In certain examples, the CRM system 500 can include only a single lead, such as 508B, or can include only two leads, such as 508A and 508B.

The lead 508A can include a proximal end that can be configured to connect to IMD 510 and a distal end that can be configured to be placed at a target location such as in the right atrium (RA) 531 of the heart 505. The lead 508A can have a first pacing-sensing electrode 551 that can be located at or near its distal end, and a second pacing-sensing electrode 552 that can be located at or near the electrode 551. The electrodes 551 and 552 can be electrically connected to the IMD 510 such as via separate conductors in the lead 508A, such as to allow for sensing of the right atrial activity and optional delivery of atrial pacing pulses. The lead 508B can be a defibrillation lead that can include a proximal end that can be connected to IMD 510 and a distal end that can be placed at a target location such as in the right ventricle (RV) 532 of heart 505. The lead 508B can have a first pacing-sensing electrode 552 that can be located at distal end, a second pacing-sensing electrode 553 that can be located near the electrode 552, a first defibrillation coil electrode 554 that can be located near the electrode 553, and a second defibrillation coil electrode 555 that can be located at a distance from the distal end such as for superior vena cava (SVC) placement. The electrodes 552 through 555 can be electrically connected to the IMD 510 such as via separate conductors in the lead 508B. The electrodes 552 and 553 can allow for sensing of a ventricular electrogram and can optionally allow delivery of one or more ventricular pacing pulses, and electrodes 554 and 555 can allow for delivery of one or more ventricular cardioversion/defibrillation pulses. In an example, the lead 508B can include only three electrodes 552, 554 and 555. The electrodes 552 and 554 can be used for sensing or delivery of one or more ventricular pacing pulses, and the electrodes 554 and 555 can be used for delivery of one or more ventricular cardioversion or defibrillation pulses. The lead 508C can include a proximal end that can be connected to the IMD 510 and a distal end that can be configured to be placed at a target location such as in a left ventricle (LV) 534 of the heart 505. The lead 508C may be implanted through the coronary sinus 533 and may be placed in a coronary vein over the LV such as to allow for delivery of one or more pacing pulses to the LV. The lead 508C can include an electrode 561 that can be located at a distal end of the lead 508C and another electrode 562 that can be located near the electrode 561. The electrodes 561 and 562 can be electrically connected to the IMD 510 such as via separate conductors in the lead 508C such as to allow for sensing of the LV electrogram and optionally allow delivery of one or more resynchronization pacing pulses from the LV.

The IMD 510 can include an electronic circuit that can sense a physiologic signal, such as via one or more of the physiologic sensors 204-222 as discussed above with reference to FIG. 2. In an example, the physiologic signal can include an electrogram or a signal representing mechanical function of the heart 505. The hermetically sealed can 512 may function as an electrode such as for sensing or pulse delivery. For example, an electrode from one or more of the leads 508A-C may be used together with the can 512 such as for unipolar sensing of an electrogram or for delivering one or more pacing pulses. A defibrillation electrode from the lead 508B may be used together with the can 512 such as for delivering one or more cardioversion/defibrillation pulses. In an example, the IMD 510 can sense impedance such as between electrodes located on one or more of the leads 508A-C or the can 512. The IMD 510 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 510 can be configured to inject current between an electrode on the RV lead 508B and the can 512, and to sense the resultant voltage between the same electrodes or between a different electrode on the RV lead 508B and the can 512. A physiologic signal can be sensed from one or more physiologic sensors that can be integrated within the IMD 510. The IMD 510 can also be configured to sense a physiologic signal from one or more external physiologic sensors or one or more external electrodes that can be coupled to the IMD 510. Examples of the physiologic signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

The CRM system 500 can include a patient chronic condition-based HF assessment circuit, such as illustrated in the commonly assigned Qi An et al., U.S. application Ser. No. 14/55,392, incorporated herein by reference in its entirety. The patient chronic condition-based HF assessment circuit can include a signal analyzer circuit and a risk stratification circuit. The signal analyzer circuit can receive patient chronic condition indicators and one or more physiologic signals from the patient, and select one or more patient-specific sensor signals or signal metrics from the physiologic signals. The signal analyzer circuit can receive the physiologic signals from the patient using the electrodes on one or more of the leads 508A-C, or physiologic sensors deployed on or within the patient and communicated with the IMD 510. The risk stratification circuit can generate a composite risk index indicative of the probability of the patient later developing an event of worsening of HF (e.g., an HF decompensation event) such as using the selected patient-specific sensor signals or signal metrics. The HF decompensation event can include one or more early precursors of an HF decompensation episode, or an event indicative of HF progression such as recovery or worsening of HF status.

The external system 520 can allow for programming of the IMD 510 and can receives information about one or more signals acquired by IMD 510, such as can be received via a communication link 503. The external system 520 can include a local external IMD programmer. The external system 520 can include a remote patient management system that can monitor patient status or adjust one or more therapies such as from a remote location.

The communication link 503 can include one or more of an inductive telemetry link, a radio-frequency telemetry link, or a telecommunication link, such as an internet connection. The communication link 503 can provide for data transmission between the IMD 510 and the external system 520. The transmitted data can include, for example, real-time physiologic data acquired by the IMD 510, physiologic data acquired by and stored in the IMD 510, therapy history data or data indicating IMD operational status stored in the IMD 510, one or more programming instructions to the IMD 510 such as to configure the IMD 510 to perform one or more actions that can include physiologic data acquisition such as using programmably specifiable sensing electrodes and configuration, device self-diagnostic test, or delivery of one or more therapies.

The patient chronic condition-based HF assessment circuit, or other assessment circuit, may be implemented at the external system 520, which can be configured to perform HF risk stratification such as using data extracted from the IMD 510 or data stored in a memory within the external system 520. Portions of patient chronic condition-based HF or other assessment circuit may be distributed between the IMD 510 and the external system 520.

Portions of the IMD 510 or the external system 520 can be implemented using hardware, software, or any combination of hardware and software. Portions of the IMD 510 or the external system 520 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 510, the CRM system 500 could include a subcutaneous medical device (e.g., subcutaneous ICD, subcutaneous diagnostic device), wearable medical devices (e.g., patch based sensing device), or other external medical devices.

Figure 6:
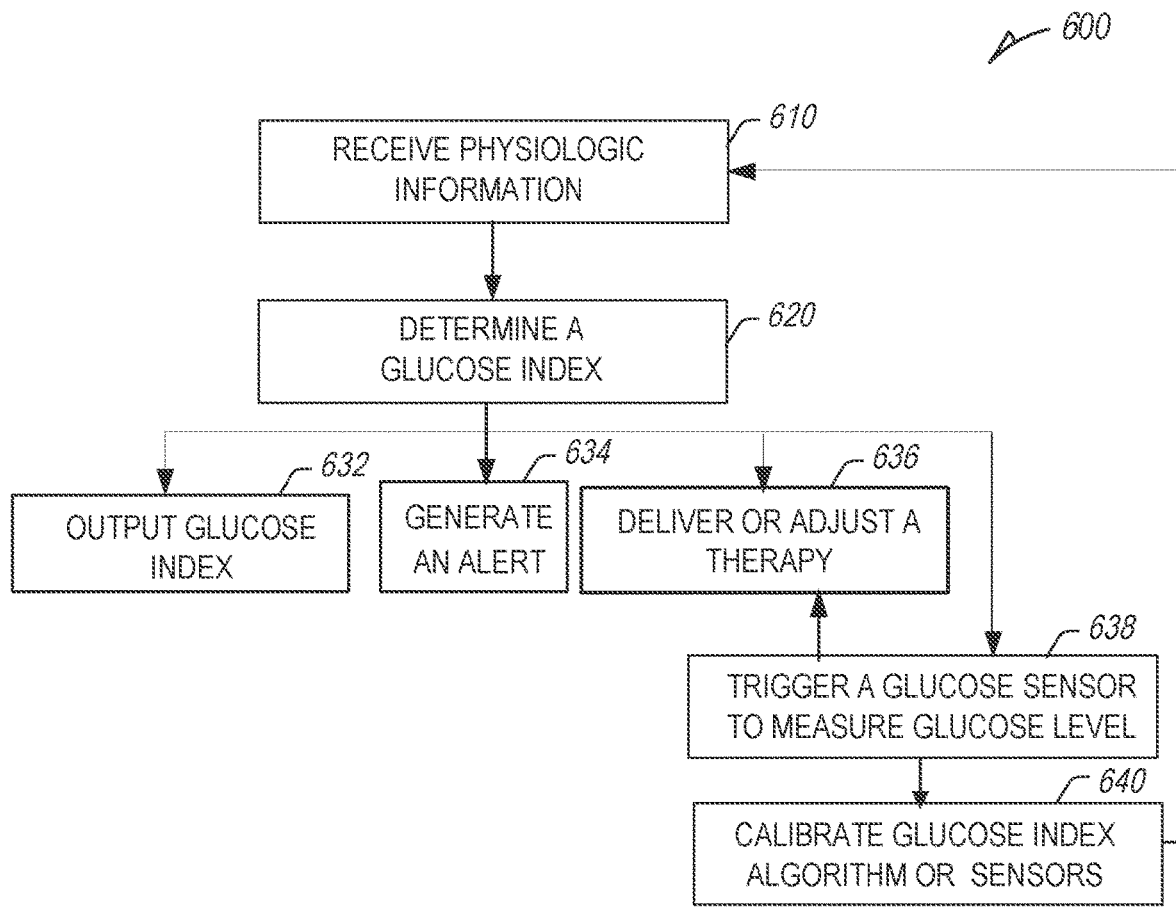
FIG. 6 illustrates an example of a method of monitoring and assessing blood glucose in a patient.

FIG. 6 illustrates generally an example of a method 600 of monitoring blood glucose level in a patient. The method 600 may be implemented in and executed by an ambulatory medical device such as an implantable or wearable medical device, or in a remote patient management system. In an example, the method 600 may be implemented in and executed by the AMD 202, the glucose management system 300 or 400, or the IMD 510.

The method 600 commences at 610, where physiologic information may be received from the patient, such as using two or more physiologic sensors. Such physiologic information may be indicative of or correlated to patient physiologic responses, symptoms, or conditions associated with abnormal blood glucose level, such as hyper- or hypoglycemia. By way of non-limiting example and as described above with reference to FIG. 2, the physiologic information may include respiration information (e.g., respiration rate, tidal volume, RSBI, dyspnea or tachypnea, etc.), heart sound information (e.g., intensity or timing measurements of one or more of S1, S2, S3, or S4 heart sound components), impedance information (e.g., blood impedance or interstitial fluid impedance), cardiac electrical information (e.g., ECG, EGM, heart rate, heart rate variability, cardiac arrhythmias, etc.), physical activity and motion information, posture or position information, or pressure information (e.g., blood pressure), among others. The physiologic information sensed from each sensor, individually or in combination, may be used to detect one or more of one or more of cardiac response, autonomic response, adrenal response, respiratory response, or impedance response (e.g., blood or interstitial fluid impedance) to glucose level change.

At 620, a glucose index may be determined using the received physiologic information, such as using the assessment circuit 304. In an example, the glucose index can be generated using an algorithm that computes a composite of physiologic information sensed from two or more physiologic sensors. The composite includes a linear or a non-linear combination (e.g., weighted combination) of the received physiologic information. The glucose index may be compared to one or more threshold to determine an indication of hyper- or hypoglycemia. In an example, the thresholds can also be customized according to personal condition or tolerance level. One or more diagnostic or therapeutic parameters (e.g., composite physiologic parameters, stratifiers, one or more electrostimulation parameters, etc.) may be generated using the received physiologic information. In an example, an optimized therapy delivery parameter may be determined using the glucose index, such as drug type, dosage, or timing of the drug therapy.

The determined glucose index may be used in one or more of the processes 632, 634, 636, or 638. At 632, the glucose index may be output to a user or a process, such as being displayed on a display unit of a user interface included in the external or remote system 404 or the external system 520. Other information, including at least portions of the received physiologic information, features or metrics generated from the received physiologic information, historical trends, and patient symptoms and condition may also be provided to the user (e.g., a clinician).

At 634, an alert or notification may be generated and provided to user (e.g., a patient, a clinician, or a caregiver) about the determined abnormality in patient glucose level. A recommendation may be provided to the user to take further glucose test (e.g., a finger prick test or a glucose strip test) to confirm the abnormality of glucose level, consult with a caregiver, take or adjust medication (e.g., dosage or timing change, change in prescribed drug, etc.), manage lifestyle, assess comorbidity, receive intervention to manage or prevent major adverse cardiovascular events and/or cardiovascular mortality, among other standards of medical care in diabetes.

At 636, intervention or therapy may be initiated or adjusted when the glucose index satisfies a specific condition, such as exceeding a first threshold and indicating hyperglycemia, or falling below a second threshold and indicating hypoglycemia. The therapy may include drug therapy, such as insulin to regular patient glucose level, or other drugs to alleviate symptoms, inflammation, or other adverse effects associated with hyper- or hypoglycemia (e.g., pain-relief drugs to remedy diabetic neuropathy). In some instances, the therapy may be delivered using the drug delivery device 406. In other instances, the therapy may be administered by the patient or caregiver using oral medication, a shot of insulin, among other treatment options. In an example, an optimized delivery parameter may be determined using the glucose index, and the drug therapy may be delivered according to the optimized delivery parameter. Additionally or alternatively, the therapy may include electrical therapy, such as electrostimulation therapy, which may be provided by the AMD 402 or the IMD 510. An optimized electrostimulation parameter may be determined using the glucose index, and electrostimulation therapy may be delivered to a patient according to the optimized electrostimulation parameter.

At 638, the determined glucose index may be used to trigger a glucose test such as to confirm or reject the multi-sensed based early warning of glucose level abnormality. In an example, a notification of patient determined glucose index may be presented to the patient or a caregiver, who can then initiate the glucose test. In another example, the determined glucose index may automatically trigger a glucose sensor to perform the test. The glucose test can be invasive or noninvasive. The glucose test can include a conventional finger prick test or glucose strip test, or involve a continuous glucose monitor such as the CGM 405 as illustrated in FIG. 4 that involves a wearable or subcutaneously implantable glucose sensor. At 640, the glucose measurements obtained from the finger prick test or glucose strip test, or from the continuous glucose monitor may be used to calibrate the glucose index algorithm, such as by adjusting the weights for individual sensors, or the method of combining the sensor measurements to determine a composite risk score, or to adjust sensor operations (e.g., sensing configuration, timing, sampling rate, duration, etc.) for collecting physiologic information. The method then returns to receiving additional physiologic information at 610 using the adjusted physiologic sensor operations, and determining the glucose index at 620 using the calibrated glucose index algorithm.

Figure 7:
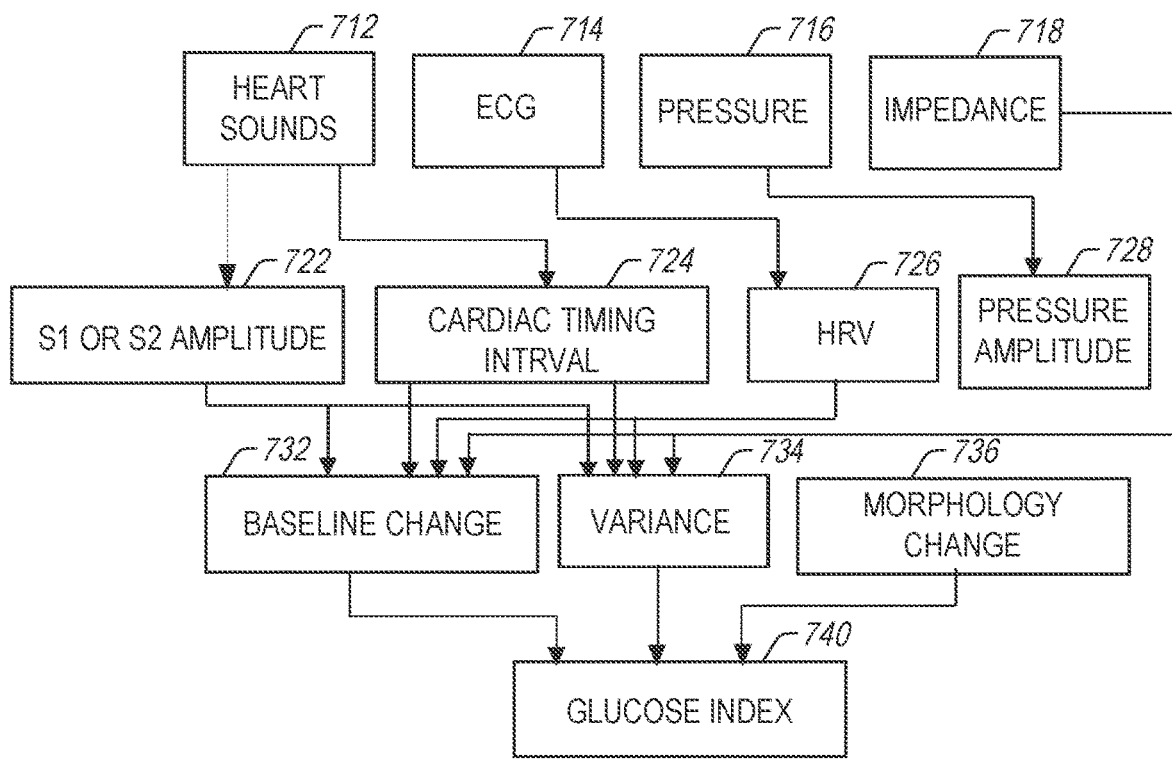
FIG. 7 illustrates an example of multi-sensor algorithm for generating a glucose index using physiologic information correlated to, but different from, a direct measurement of glucose level.

FIG. 7 is a diagram illustrating an example of multi-sensor algorithm for generating a glucose index using physiologic information sensed by two or more physiologic sensors. The physiologic information can be correlated to, but different from, a direct glucose level measurement such as sensed by a glucose sensor. The multi-sensor algorithm can be implemented in and executed by, for example, the glucose index generator 305. By way of non-limiting example and as illustrated in FIG. 7, the physiologic information may include information of heart sounds 712, ECG 714, pressure 716, and impedance 718. One or more signal features may be generated from each of the physiologic information 712-718. For example, S1 or S2 heart sound amplitudes 722 and cardiac timing intervals 724 may be generated using the heart sounds information 712. The cardiac timing interval may be measured between a cardiac electrical event such as detected from the cardiac electrical signal and a mechanical event such as detected from the HS signal. Examples of the CTI may include a pre-ejection period (PEP), a systolic timing interval (STI), a left ventricular ejection time (LVET), or a diastolic timing interval (DTI), among others. Heart rate variability (HRV) feature 726 may be generated using the ECG 714. Pressure amplitudes 728, such as systolic pressure and diastolic pressure amplitudes, may be generated using the pressure signal 716. The physiologic information and the generated signal features may represent patient physiologic responses to a change in blood glucose level. For example, the heart sounds 712 and the ECG 714 may represent cardiac response to glucose level change; the pressure 716 may represent adrenal response to glucose level change; and the HRV 726 may represent autonomic response to glucose level change. The multi-sensor algorithm combines various physiologic responses Statistical measurements of the signal features 722-728 may be computed. Examples of the statistical measurements may include changes from baseline levels 732, and variance 734 (or other second-order statistics) of the respective signal features 722-728, and of the impedance information 718. In an example, the change from baseline level 732 may be computed in a programmable time period, such as approximately between 1 and 24 hours. In an example, the variance 734 may be computed in a short programmable period, such as approximately one minute to one hour. The computed statistical measurements, including the baseline levels 732 and variance 734 of various signal features and the impedance may be combined using a linear or nonlinear method to produce a glucose index 740. As illustrated in FIG. 7, morphology changes 736 of one or more of the heart sounds 712, ECG 714, pressure 716, or impedance 718 may also be used to generate the glucose index 740. The glucose index 740 thus generated can be a surrogate to direct glucose level measurement, or as an early indicator of hyper- or hypoglycemia. The glucose index 740 generated using the multi-sensor algorithm as described herein is a composite indicator of patient cardiac, autonomic, adrenal, and other physiologic responses to abnormal glucose level, and is more accurate and reliable in detecting abnormal glucose level (e.g., hyper- or hypoglycemia) than a single sensor approach. In some examples, the glucose index 740 may be used to trigger a separate glucose sensor that directly measures a glucose level.

Figure 8:
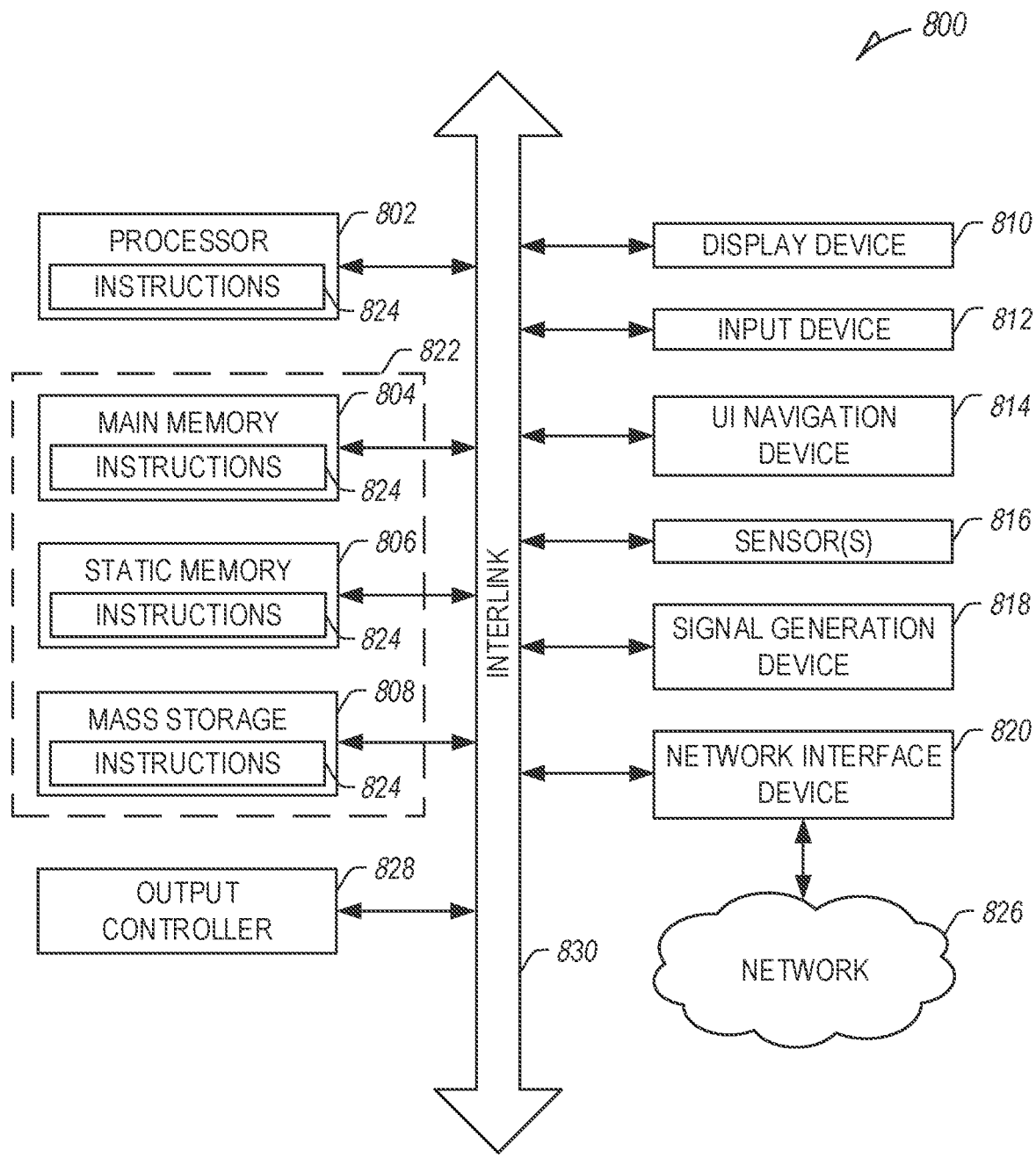
FIG. 8 illustrates a block diagram of an example machine upon which any one or more of the techniques (e.g., methodologies) discussed herein may perform.

FIG. 8 illustrates a block diagram of an example machine 800 upon which any one or more of the techniques (e.g., methodologies) discussed herein may perform. Portions of this description may apply to the computing framework of one or more of the medical devices described herein, such as the IMD, the external programmer, etc.

Examples, as described herein, may include, or may operate by, logic or a number of components, or mechanisms in the machine 800. Circuitry (e.g., processing circuitry) is a collection of circuits implemented in tangible entities of the machine 800 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 800 follow.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 800 may include a hardware processor 802 (e.g., a central processing unit (CPU), a graphics processing unit (GPU), a hardware processor core, or any combination thereof), a main memory 804, a static memory (e.g., memory or storage for firmware, microcode, a basic-input-output (BIOS), unified extensible firmware interface (UEFI), etc.) 806, and mass storage 808 (e.g., hard drive, tape drive, flash storage, or other block devices) some or all of which may communicate with each other via an interlink (e.g., bus) 830. The machine 800 may further include a display unit 810, an alphanumeric input device 812 (e.g., a keyboard), and a user interface (UI) navigation device 814 (e.g., a mouse). In an example, the display unit 810, input device 812, and UI navigation device 814 may be a touch screen display. The machine 800 may additionally include a signal generation device 818 (e.g., a speaker), a network interface device 820, and one or more sensors 816, such as a global positioning system (GPS) sensor, compass, accelerometer, or one or more other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 802, the main memory 804, the static memory 806, or the mass storage 808 may be, or include, a machine-readable medium 822 on which is stored one or more sets of data structures or instructions 824 (e.g., software) embodying or utilized by any one or more of the techniques or functions described herein. The instructions 824 may also reside, completely or at least partially, within any of registers of the processor 802, the main memory 804, the static memory 806, or the mass storage 808 during execution thereof by the machine 800. In an example, one or any combination of the hardware processor 802, the main memory 804, the static memory 806, or the mass storage 808 may constitute the machine-readable medium 822. While the machine-readable medium 822 is illustrated as a single medium, the term "machine-readable medium" may include a single medium or multiple media (e.g., a centralized or distributed database, and/or associated caches and servers) configured to store the one or more instructions 824.

The term "machine-readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may be further transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system comprising:
an ambulatory medical device configured to receive multiple types of physiologic information correlated to, and different from, a direct glucose level measurement, the physiologic information respectively sensed by two or more physiologic sensors from a patient, the multiple types of physiologic information comprising at least one of cardiac electrical information indicative of an electrical activity of a heart or tissue of the patient or cardiac mechanical information indicative of a mechanical activity of the heart or tissue of the patient; and
an assessment circuit configured to:
receive information about patient risk of abnormal blood glucose level including at least a first risk level and a second risk level different from the first risk level;
select a first type or portion of the multiple types of received physiologic information based on the received first risk level, and select a second type or portion of the multiple types of received physiologic information based on the received second risk level, the second type or portion different from the first type or portion;
determine a glucose index indicative of an abnormal blood glucose level for the patient, including determining a first glucose index using the selected first type or portion of the multiple types of received physiologic information, and determining a second glucose index using the selected second type or portion of the multiple types of received physiologic information; and
provide an output to trigger measurement from a third sensor, separate from the two or more physiological sensors, configured to directly measure a glucose level based on the determined glucose index satisfying a condition.

2. The system of claim 1,
wherein to select the first type or portion of the multiple types of received physiologic information includes to select a first group of the two or more physiologic sensors,
wherein to select the second type or portion of the multiple types of received physiologic information includes to select a second group of the two or more physiologic sensors different from the first group of the two or more physiologic sensors.

3. The system of claim 1, wherein the third sensor comprises a glucose sensor separate from the two or more physiologic sensors, and
wherein the assessment circuit is configured to trigger the glucose sensor to directly measure the glucose level when the determined glucose index satisfies the condition.

4. The system of claim 3, comprising an implantable or wearable glucose monitor communicatively coupled to the ambulatory medical device, the implantable or wearable glucose monitor including the glucose sensor configured to directly measure the glucose level when the determined glucose index satisfies the condition.

5. The system of claim 3, comprising a calibration circuit configured to, using the measured glucose level, adjust a sensor configuration of at least one of the two or more physiologic sensors to sense physiologic information or to calibrate an algorithm for generating the glucose index.

6. The system of claim 1, wherein the ambulatory medical device includes a cardiac sensor configured to receive the cardiac electrical or the mechanical information of the patient, and the assessment circuit is configured to determine the glucose index using the received cardiac electrical or mechanical information.

7. The system of claim 6, wherein the cardiac sensor includes electrodes configured to sense the cardiac electrical information including one or more of a heart rate, a heart rate variability, a Q-T interval, or a cardiac arrhythmia, and the assessment circuit is configured to determine the glucose index using the sensed cardiac electrical information.

8. The system of claim 1, wherein the ambulatory medical device includes a heart sound sensor configured to receive heart sound information of the patient, and the assessment circuit is configured to determine the glucose index using the received heart sound information.

9. The system of claim 1, wherein the ambulatory medical device includes an impedance sensor configured to receive impedance information of the patient, and the assessment circuit is configured to determine the glucose index using the received impedance information,
wherein the impedance information includes interstitial fluid impedance or blood impedance.

10. The system of claim 1, wherein the assessment circuit is configured to generate a composite risk score using a combination of the received physiologic information respectively sensed by the two or more physiologic sensors each weighted by respective weights, and to determine the glucose index using a portion of the received physiologic information selected based on the composite risk score.

11. The system of claim 10, wherein the assessment circuit is configured to adjust one or more of the respective weights based on the composite risk score, the respective weights indicative of responses of the two or more physiological sensors to abnormal glucose level.

12. The system of claim 1, comprising a drug delivery device configured to control delivery of a glucose therapy to the patient according to a delivery parameter,
wherein the assessment circuit is configured to adjust the delivery parameter using the determined glucose index.

13. The system of claim 1, comprising a therapy circuit configured to deliver electrostimulation to the patient according to a therapy parameter,
wherein the assessment circuit is configured to adjust the therapy parameter using the determined glucose index.

14. A method comprising:
receiving multiple types of physiologic information via an ambulatory medical device, the physiologic information respectively sensed from a patient by two or more physiologic sensors, the received physiologic information correlated to, and different from, a direct glucose level measurement, the multiple types of physiologic information comprising at least one of cardiac electrical information indicative of an electrical activity of a heart or tissue of the patient or cardiac mechanical information indicative of a mechanical activity of the heart or tissue of the patient;

receiving, via an assessment circuit, information about patient risk of abnormal blood glucose level including at least a first risk level and a second risk level different from the first risk level;

selecting a first type or portion of the multiple types of received physiologic information based on the received first risk level, and selecting a second type or portion of the multiple types of received physiologic information based on the received second risk level, the second type or portion different from the first type or portion;

determining, via the assessment circuit, a glucose index indicative of an abnormal blood glucose level for the patient, including determining a first glucose index using the selected first type or portion of the multiple types of received physiologic information, and determining a second glucose index using the selected second type or portion of the multiple types of received physiologic information; and triggering measurement from a third sensor, separate from the two or more physiologic sensors, to directly measure a glucose level based on the determined glucose index satisfying a condition.

15. The method of claim 14, wherein triggering measurement from the third sensor includes triggering measurement from a glucose sensor to directly measure the glucose level when the determined glucose index satisfies the condition, wherein the glucose sensor is separate from the two or more physiologic sensors.

16. The method of claim 15, comprising adjusting a sensor configuration of at least one of the two or more physiologic sensors to sense physiologic information or calibrating an algorithm for generating the glucose index using the measured glucose level.

17. The method of claim 14, comprising delivering a glucose therapy using a drug delivery device to the patient according to a delivery parameter, and adjusting the delivery parameter using the determined glucose index.

18. The method of claim 14, comprising delivering electrostimulation to the patient according to a therapy parameter, and adjusting the therapy parameter using the determined glucose index.

19. The method of claim 14, wherein the received physiologic information includes one or more of:
cardiac electrical information sensed by a cardiac sensor;
heart sound information sensed by a heart sound sensor;
respiration information sensed by a respiration sensor;
impedance information sensed by an impedance sensor; or
pressure information sensed by a pressure sensor,
wherein selecting the first type or portion of the multiple types of received physiologic information includes selecting a first group of the two or more physiologic sensors,
wherein selecting the second type or portion of the multiple types of received physiologic information includes selecting a second group of the two or more physiologic sensors different from the first group of the two or more physiologic sensors.

20. The method of claim 14, comprising:
generating a composite risk score using a combination of the received physiologic information respectively sensed from two or more physiologic sensors each weighted by respective weights; and
determining the glucose index using a portion of the received physiologic information selected based on the composite risk score.

* * * * *